(12) United States Patent
Jubran et al.

(10) Patent No.: US 6,340,548 B1
(45) Date of Patent: Jan. 22, 2002

(54) ORGANOPHOTORECEPTORS FOR ELECTROPHOTOGRAPHY FEATURING NOVEL CHARGE TRANSPORT COMPOUNDS

(75) Inventors: Nusrallah Jubran, Saint Paul; Zbigniew Tokarski; Terrance P. Smith, both of Woodbury, all of MN (US)

(73) Assignee: Imation Corp., Oakdale, MN (US)

( * ) Notice: Subject to any disclaimer, the term of this patent is extended or adjusted under 35 U.S.C. 154(b) by 0 days.

(21) Appl. No.: 09/526,789

(22) Filed: Mar. 16, 2000

(51) Int. Cl.$^7$ .................. G03G 5/047; G03G 15/00; C07P 209/82
(52) U.S. Cl. ............ 430/58.45; 430/56; 430/58.6; 430/79; 399/162; 548/440; 548/444
(58) Field of Search ................. 430/56, 58.45, 430/58.6, 79, 83; 548/440, 444; 399/162

(56) References Cited

U.S. PATENT DOCUMENTS

| | | | |
|---|---|---|---|
| 4,216,286 A | 8/1980 | Greene et al. | 430/203 |
| 4,256,821 A | 3/1981 | Enomoto et al. | 430/79 |
| 4,278,747 A | 7/1981 | Murayama et al. | 430/82 |
| 4,338,388 A | 7/1982 | Sakai et al. | 430/70 |
| 4,365,014 A | 12/1982 | Sakai et al. | 430/79 |
| 4,439,509 A | 3/1984 | Schank | 430/132 |
| 4,451,549 A | 5/1984 | Kato | 430/134 |
| 4,454,212 A | 6/1984 | Sakai et al. | 430/79 |
| 4,470,861 A | 9/1984 | Kravig et al. | 156/222 |
| 4,565,760 A | 1/1986 | Schank | 430/66 |
| 4,595,602 A | 6/1986 | Schank | 430/132 |
| 4,606,934 A | 8/1986 | Lee et al. | 430/76 |
| 4,784,929 A | 11/1988 | Ueda | 430/81 |
| 4,923,775 A | 5/1990 | Schank | 430/66 |
| 4,968,579 A | 11/1990 | Kimoto et al. | 430/134 |
| 4,988,596 A | 1/1991 | Ueda | 430/58.45 |
| 5,089,366 A | 2/1992 | Haino et al. | 430/73 |
| 5,098,810 A | 3/1992 | Mizuguchi et al. | 430/78 |
| 5,124,220 A | 6/1992 | Brown et al. | 430/67 |
| 5,158,850 A | 10/1992 | Sasaki et al. | 430/71 |
| 5,284,728 A | 2/1994 | Murayama et al. | 430/73 |
| 5,422,210 A | 6/1995 | Murayama et al. | 430/66 |
| 5,622,800 A | 4/1997 | Ando et al. | 430/83 |
| 5,650,253 A | 7/1997 | Baker et al. | 430/119 |
| 5,659,851 A | 8/1997 | Moe et al. | 399/165 |
| 5,756,248 A | 5/1998 | Tanaka et al. | 430/83 |
| 5,824,444 A * | 10/1998 | Kinoshita et al. | 430/59 |
| 5,851,712 A * | 12/1998 | Muto et al. | 430/83 |
| 5,902,884 A | 5/1999 | Bauer et al. | 548/447 |
| 6,066,426 A * | 5/2000 | Mott et al. | 430/58.2 |
| 6,140,004 A * | 10/2000 | Mott et al. | 430/132 |
| 6,165,930 A * | 12/2000 | Stewart | 502/152 |
| 6,180,305 B1 * | 1/2001 | Ackley et al. | 430/66 |
| 6,214,503 B1 * | 4/2001 | Gaidelis et al. | 430/58.45 |

FOREIGN PATENT DOCUMENTS

| | | | |
|---|---|---|---|
| JP | 55-74547 | * | 6/1980 |
| JP | 58-2849 | | 1/1983 |
| JP | 1-234855 | | 9/1989 |
| WO | WO 00/22483 | | 4/2000 |

OTHER PUBLICATIONS

English Abstract of JP 55074547A2, Issued on Jun. 5, 1980.*
Esp@cenent Database —12 English Abstract of JP 57158645, Pub Sep. 1982.*
English Abstract of JP 59 078363A2 Issued May 1984.*
Esp@cenet Database —12 English Abstract of JP 2082263, Pub Mar. 1990.*
Esp@cenet Database—12 English Abstract of JP 2245763, Pub Oct. 1990.*
Esp@cenet Database—12 English Abstract of JP 4110857, Pub Apr. 1992.*
Esp@cenet Database—12 English Abstract of JP 4116566, Pub Apr. 1992.*
English Translation of JP 62116943, Pub May 1987, Provided by Applicants.*
English Translation of JP 60–237,453, pub. Nov. 1985, Provided by Applicants.*
Japanese Patent Office English Abstract of JP 62121460, Copyright 1987.*
Japanese Patent Office English Abstract of JP 02129651, Copyright 1990.*
Japanese Patent Office English Abstract of JP 10221870, Copyright 1998.*
Japanese Patent Office English Abstract of JP 06175381, Copyright 1994.*
Derwent Abstract Acc. No. 1980–50876C of JP 55074547, Jun. 5, 1980.*
E. Gutoff, *Modern Coating and Drying Technology*, VCH Publishers, Inc. New York, 1992, pp. 117–120.
Zhang, Wada and Sasabe, *J. Polym. Sci. Part A: Polym. Chem.*, 1996, 34, 2289–2298.

* cited by examiner

*Primary Examiner*—Janis L. Dote
(74) *Attorney, Agent, or Firm*—Amelia A. Buharin

(57) ABSTRACT

Organic photoreceptors that include a charge transport compound, a charge generating compound, and an electroconductive support in which the charge transport compound is a novel aryl hydrazone-functional carbazole compound.

13 Claims, No Drawings

ORGANOPHOTORECEPTORS FOR ELECTROPHOTOGRAPHY FEATURING NOVEL CHARGE TRANSPORT COMPOUNDS

BACKGROUND

This invention relates to organic photoreceptors suitable for use in electrophotography.

In electrophotography, a photoreceptor in the form of a plate, belt, or drum having an electrically insulating photoconductive element on an electrically conductive substrate is imaged by first uniformly electrostatically charging the surface of the photoconductive layer, and then exposing the charged surface to a pattern of light. The light exposure selectively dissipates the charge in the illuminated areas, thereby forming a pattern of charged and discharged areas. A liquid or solid toner is then deposited in either the charged or discharged areas to create a toned image on the surface of the photoconductive layer. The resulting visible toner image can be transferred to a suitable receiving surface such as paper. The imaging process can be repeated many times.

Both single layer and multilayer photoconductive elements have been used. In the single layer embodiment, a charge transport material and a charge generating material are combined with a polymeric binder and then deposited on the electrically conductive substrate. In the multilayer embodiment, the charge transport material and charge generating material are in the form of separate layers, each of which can optionally be combined with a polymeric binder, deposited on the electrically conductive substrate. Two arrangements are possible. In one arrangement (the "dual layer" arrangement), the charge generating layer is deposited on the electrically conductive substrate and the charge transport layer is deposited on top of the charge generating layer. In an alternate arrangement (the "inverted dual layer" arrangement), the order of the charge transport layer and charge generating layer is reversed.

In both the single and multilayer photoconductive elements, the purpose of the charge generating material is to generate charge carriers (i.e., holes and electrons) upon exposure to light. The purpose of the charge transport material is to accept these charge carriers and transport them through the charge transport layer in order to discharge a surface charge on the photoconductive element.

To produce high quality images, particularly after multiple cycles, it is desirable for the charge transport material to form a homogeneous solution with the polymeric binder and remain in solution. In addition, it is desirable to maximize the amount of charge which the charge transport material can accept (indicated by a parameter known as the acceptance voltage or "$V_{acc}$"), and to minimize retention of that charge upon discharge (indicated by a parameter known as the residual voltage or "$V_{res}$").

Liquid toners generally produce superior images compared to dry toners. However, liquid toners also can facilitate stress crazing in the photoconductive element. Stress crazing, in turn, leads to printing defects such as increased background. It also degrades the photoreceptor, thereby shortening its useful lifetime. The problem is particularly acute when the photoreceptor is in the form of a flexible belt included in a compact imaging machine that employs small diameter support rollers (e.g., having diameters no greater than about 40 mm) confined within a small space. Such an arrangement places significant mechanical stress on the photoreceptor, and can lead to degradation and low quality images.

SUMMARY

In a first aspect, the invention features an organic photoreceptor that includes:

(a) a change transport compound having the formula

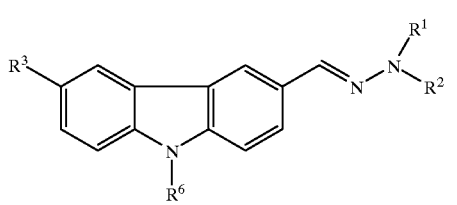

(1)

where $R^1$ and $R^2$, independently, are hydrogen, an alkyl group (e.g., a $C_1$–$C_6$ alkyl group), or an aryl group (e.g., a phenyl or naphthyl group);

$R^3$ is hydrogen or a hydrazone group having the formula

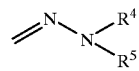

$R^4$ and $R^5$, independently, are hydrogen, an alkyl group (e.g., a $C_1$–$C_6$ alkyl group), or an aryl group (e.g., a phenyl or naphthyl group);

$R^6$ is an aryl group (e.g., a phenyl or naphthyl group); straight or branched alkyl group having at least 7 carbon atoms; a group having the formula —$(CH_2)_n$—Ar where n is at least 3, Ar represents an aryl group (e.g., a phenyl or naphthyl group), and one or more methylene groups is optionally substituted with a hetero atom; or a carbazole group having the formula

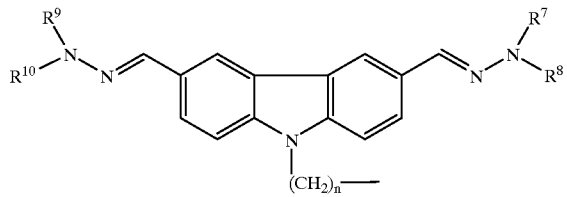

where $R^7$, $R^8$, $R^9$, and $R^{10}$, independently, are hydrogen, an alkyl group (e.g., a $C_1$–$C_6$ alkyl group), or an aryl group (e.g., a phenyl or naphthyl group); n is at least 3; and one or more methylene groups is optionally substituted with a heteroatom;

(b) a charge generating compound; and
(c) an electroconductive substrate.

The organic photoreceptor may be provided in the form of a flexible belt. In one embodiment, the organic photoreceptor includes: (a) a charge transport layer comprising at least one of the charge transport compounds and a polymeric binder; (b) a charge generating layer comprising the charge generating compound and a polymeric binder; and (c) the electroconductive substrate. The charge transport layer preferably has a glass transition temperature of at least about 80° C. In one embodiment, the charge transport layer includes two of the charge transport compounds in a ratio with one another of about 9:1 to about 1:1. The charge transport layer may be intermediate the charge generating layer and the electroconductive substrate. Alternatively, the charge generating layer may be intermediate the charge transport layer and the electroconductive substrate.

In one preferred embodiment, a charge transport compound is selected in which $R^3$ is a hydrazone group, $R^4$ is a methyl group, and R⁵ is a phenyl group. Specific examples of suitable charge transport compounds have the following formulae:
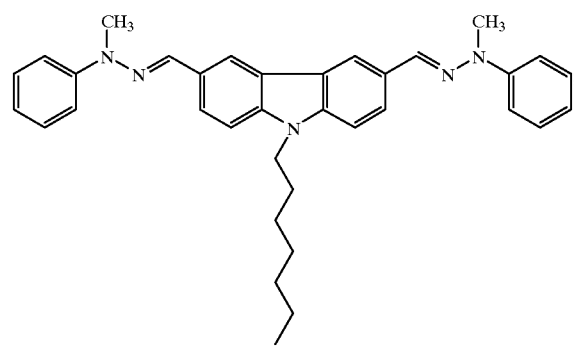
(2)
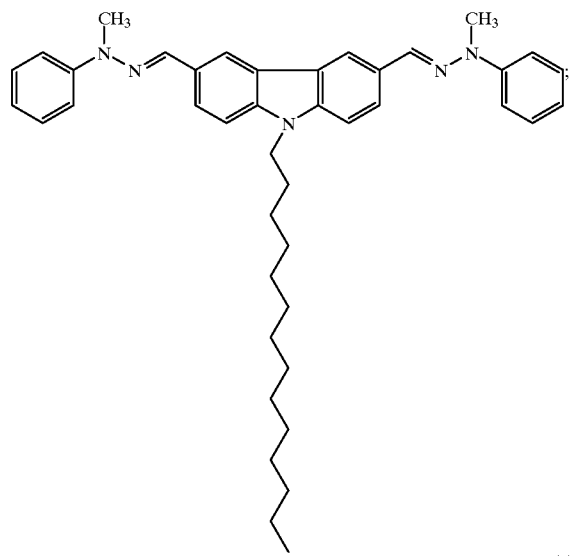
(3)
(4)
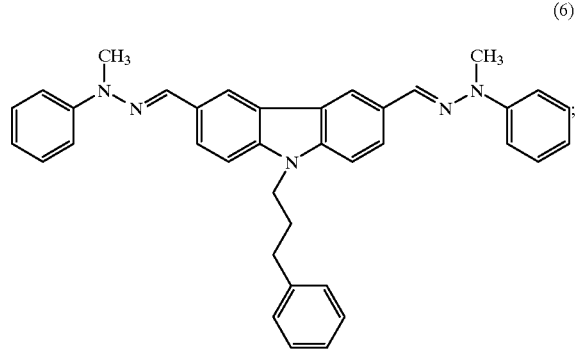
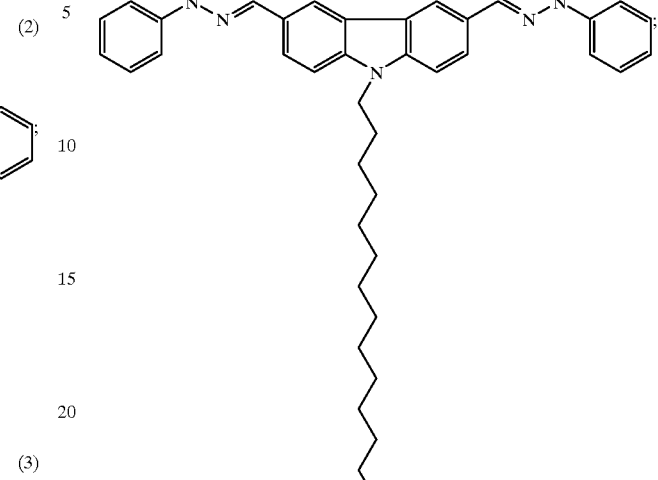
(5)
(6)
(7)
(9)
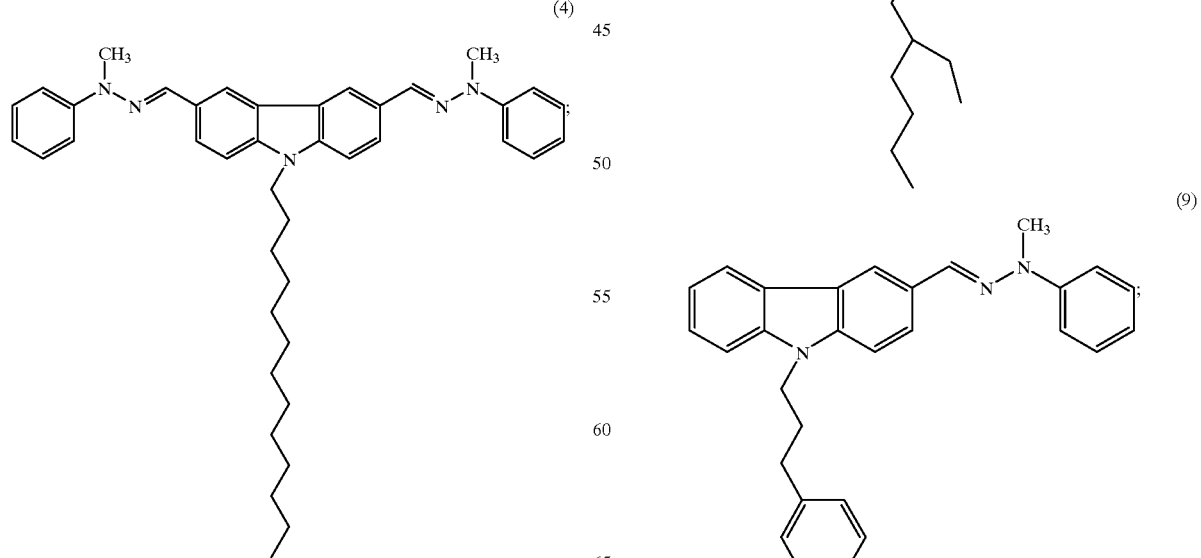

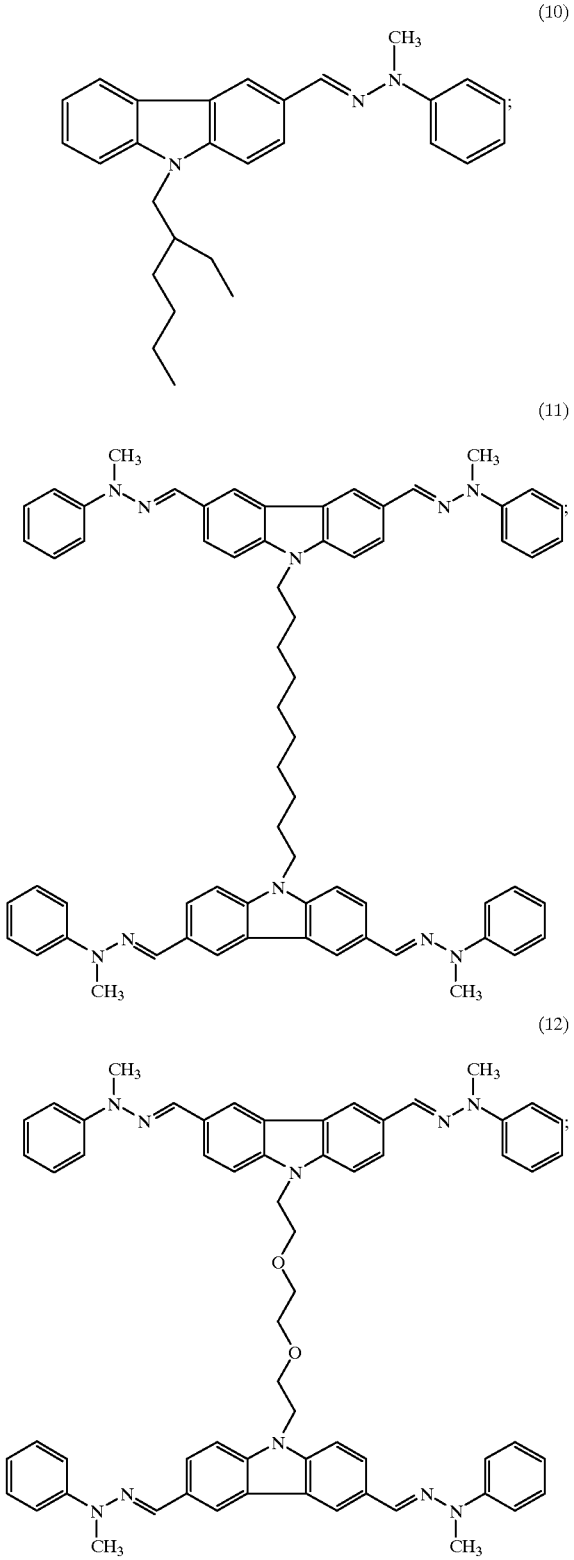

The charge transport compounds may be used alone or in combination with each other. The invention also features the charge transport compounds themselves.

In a second aspect, the invention features an electrophotographic imaging apparatus that includes (a) a plurality of support rollers and (b) the above-described organic photoreceptor in the form of a flexible belt supported by the support rollers. Preferably, at least one of the support rollers has a diameter no greater than about 40 mm. The apparatus preferably further includes a liquid toner dispenser.

In a third aspect, the invention features an electrophotographic imaging process that includes (a) applying an electrical charge to a surface of the above-described organic photoreceptor; (b) imagewise exposing the surface of the organic photoreceptor to radiation to dissipate charge in selected areas and thereby form a pattern of charged and discharged areas on the surface; (c) contacting the surface with a liquid toner that includes a dispersion of colorant particles in an organic liquid to create a toned image; and (d) transferring the toned image to a substrate.

In a preferred embodiment, the organic photoreceptor is in the form of a flexible belt, e.g., a flexible belt supported by a plurality of support rollers, at least one of which has a diameter no greater than about 40 mm.

The invention provides organic photoreceptors featuring a combination of good mechanical properties and electrostatic properties. These photoreceptors can be used successfully with liquid toners to produce high quality images even when subjected to significant mechanical stresses encountered when the photoreceptor is in the form of a flexible belt supported by a plurality of small diameter rollers. The high quality of the images is maintained after repeated cycling.

Other features and advantages of the invention will be apparent from the following description of the preferred embodiments thereof and from the claims.

DETAILED DESCRIPTION

The invention features organic photoreceptors that include charge transport compounds having the formulae set forth in the Summary of the Invention, above. The charge transport compounds are aryl hydrazone-functional carbazoles. They are preferably prepared via N-alkylation of a carbazole, followed by a Vielsmayer reaction to form an aldehyde group on the carbazole molecule, and then reaction of the aldehyde with a hydrazine to form the final hydrazone product.

In some cases, it may be desirable to include two or more charge transport compounds in a single charge transport layer in order to increase solubility in the solvent used to prepare the layer. For example, a 1:1 mixture by weight of two charge transport compounds may be more soluble in a solvent such as tetrahydrofuran than each one individually at the same concentration. Increased solubility results in layers having improved uniformity and transparency, as well as improved electrostatic properties. Preferably, two charge transport compounds are utilized in a ratio with one another of about 9:1 to about 1:1 mixture by weight.

The organic photoreceptor may be in the form of a plate, drum, or belt, with the novel charge transport compounds being particularly useful in the case of flexible belts. The photoreceptor may include a conductive substrate and a photoconductive element in the form of a single layer that includes both the charge transport compound, the charge generating compound, and separate polymeric binder. Preferably, however, the photoreceptor includes a conductive substrate and a photoconductive element that is a bilayer construction featuring a charge generating layer and a separate charge transport layer. The charge generating layer may be located intermediate the conductive substrate and the charge transport layer. Alternatively, the photoconductive element may be an inverted construction in which the charge transport layer is intermediate the conductive substrate and the charge generating layer.

The photoreceptors are suitable for use in an imaging process with either dry or liquid toner development. Liquid toner development is generally preferred because it offers the advantages of providing higher resolution images and requiring lower energy for image fixing compared to dry toners. Examples of useful liquid toners are well-known. They typically include a colorant, a resin binder, a charge director, and a carrier liquid. A preferred resin to pigment ratio is 2:1 to 10:1, more preferably 4:1 to 8:1. Typically, the colorant, resin, and the charge director form the toner particles.

The photoreceptors are particularly useful in a compact imaging apparatus where the photoreceptor is wound around several small diameter rollers (e.g., having diameters no greater than about 40 mm). A number of apparatus designs may be employed, including, for example, the apparatus designs disclosed in U.S. Pat. No. 5,650,253 and U.S. Pat. No. 5,659,851.

The charge generating compound is a material which is capable of absorbing light to generate charge carriers, such as a dyestuff or a pigment One example of a suitable charge generating compound is a metal-free phthalocyanine pigment (e.g., PROGEN 1 x-form metal-free phthalocyanine pigment from Zeneca, Inc.). Also suitable are Y-form metal-free phthalocyanine pigments.

The binder is capable of dispersing or dissolving the charge transport compound (in the case of the charge transport layer) and the charge generating compound (in the case of the charge generating layer). Examples of suitable binders for both the charge generating layer and charge transport layer include styrenebutadiene copolymers, modified acrylic polymers, vinyl acetate polymers, styrene-alkyd resins, soya-alkyl resins, polyvinyl chloride, polyvinylidene chloride, acrylonitrile, polycarbonate, polyacrylic and methacrylic esters, polystyrene, polyesters, and combinations thereof Examples of suitable polycarbonate binders include aryl polycarbonates such as poly(4,4-dihydroxy-diphenyl-1,1-cyclohexane) ("Polycarbonate Z") and poly(Bisphenol A carbonate co-4,4'(3,3,5-trimethyl cyclohexylidene diphenol)). Another example of a useful binder is polyvinyl butyral.

Other layers that may be included in the photoreceptor include, for example, barrier layers and release layers. Examples of suitable barrier layers include crosslinkable siloxanol-colloidal silica hybrids (as disclosed, e.g., in U.S. Pat. Nos. 4,439,509; 4,606,934; 4,595,602; and 4,923,775); a coating formed from a dispersion of hydroxylated silsesquioxane and colloidal silica in an alcohol medium (as disclosed, e.g., in U.S. Pat. No. 4,565,760); a polymer resulting from a mixture of polyvinyl alcohol with methyl vinyl ether/maleic anhydride copolymer; and polyvinyl butyral crosslinked with a copolymer of maleic anhydride and methylvinyl ether (commerically available under the trade designation GANTREZ AN169) containing about 30% silica. Examples of suitable release layers include fluorinated polymers, siloxane polymers, silanes, polyethylene, and polypropylene, with crosslinked silicone polymers being preferred.

The invention will now be described further by way of the following examples.

EXAMPLES

A. Synthesis

Charge transport compounds were synthesized as follows. The number associated with each compound refers to the number of the chemical formula set forth in the Summary of the Invention, above.

Compound (2)

To a 1liter 3-neck round bottom flask equipped with reflux condenser and mechanical stirrer were added 88.69 g carbazole (0.53 mol), 100 g 1-bromoheptane (0.56 mol), 6.00 g benzyltriethyl ammonium chloride (0.026 mol) and 400 ml of toluene. The mixture was stirred at room temperature for 0.5 hr., followed by the addition of an aqueous solution of NaOH (prepared by dissolving 100 g of NaOH in 100 g water). The mixture was refluxed for 5 hr. and cooled to room temperature. The organic phase was separated and washed repeatedly with water until the pH of the washing water was neutral. The organic phase was dried over $Mg_2SO_4$, filtered, and evaporated to dryness to obtain 126 g of brown liquid (89% yield). $^1$H-NMR and IR spectra were in agreement with the structure of N-heptylcarbazole.

To a 1-liter, 3-neck round bottom flask equipped with mechanical stirrer, thermometer, and addition funnel, was added 271 ml DMF (3.5 mol). The contents were cooled in a salt/ice bath. When the temperature inside the flask reached 0° C., 326 ml of $POCl_3$ (3.5 mol) was slowly added. During the addition of $POCl_3$, the temperature inside the flask was not allowed to rise above 5° C. After the addition of $POCl_3$ was completed, the reaction mixture was allowed to warm to room temperature. 126 g of N-heptylcarbazole was then added and the flask was heated to 90° C. for 24 hr. using a heating mantle. The reaction mixture was cooled to room temperature and the solution was added slowly to a 4.5 liter beaker containing a solution of 820 g sodium acetate dissolved in 2 liters of water. The beaker was cooled in an ice bath and stirred for 3 hr. The brownish solid obtained was filtered and washed repeatedly with water, followed by a small amount of ethanol (50 ml). The resulting product was recrystallized once from toluene using activated charcoal and dried under vacuum in an oven heated at 70° C. for 6 hr to obtain 80 g (51% yield) of N-heptyl-3,6-diformyl-carbazole. $^1$H-NMR and IR spectra confirmed the presence of N-heptyl-3,6-diformyl-carbazole.

To a 250 ml 3-neck round bottom flask equipped with reflux condenser and mechanical stirrer were added 9.63 g (0.03 mol) of N-heptyl-3,6-diformylcarbazole and 100 ml toluene. Heating was applied until all solid entered into solution, then 8 drops of concentrated HCl were added, followed by the addition of a solution of 7.7 g of N-methyl-N-phenylhydrazine (0.063 mol) in 25 ml toluene. The flask was heated under reflux for 5 hr, during which a solid was formed. The flask was cooled to room temperature and the solid was filtered off, washed with toluene and ethanol, and dried in an oven at 70° C. under vacuum for 6 hr. The product was recrystallized three times from toluene using activated charcoal in all three recrystallizations. CELITE, a diatomaceous earth material, was also used in the third recrystallization. The product was dried at 70° C. under vacuum for 6 hr to obtain 10 g of Compound (2) as a light yellow solid (63% yield). $^1$H-NMR and IR were in agreement with the proposed structure.

Compound (3)

N-dodecyl carbazole was prepared from carbazole (66 g, 0.40 mol), 1-bromododecane (100 g, 0.41 mol), benzyltriethyl ammonium chloride (4.48 g, 0.02 mol), toluene (400 ml), and sodium hydroxide (200 g of 50% aqueous solution) according to the procedure described for Compound (2). The product was obtained as 115 g of brown liquid (87% yield). $^1$H-NMR and IR confirmed the structure to be N-dodecylcarbazole.

N-dodecyl-3,6-diformyl carbazole was prepared from DMF (186 ml, 2.4 mol), $POCl_3$ (224 ml, 2.4 mol), and N-dodecylcarbazole (115 g, 0.34 mol), according to the procedure described for Compound (2). The product was recrystallized once from THF/water to yield 100 g of a brown solid (75% yield). $^1$H-NMR and IR confirmed the structure to be N-dodecyl-3,6-diformylcarbazole.

Compound (3) was prepared from N-dodecyl-3,6-diformylcarbazole (11.76 g, 0.03 mol, N-methyl-N-phenylhydrazine (7.7 g, 0.063 mol), and 8 drops of conc. HCl according to the procedure described for Compound (2). The solid was recrystallized 3 times from toluene using activated charcoal. CELITE, a diatomaceous earth material, was also used in the third recrystallization. 11 g (61% yield) of Compound (3) were obtained. $^1$H-NMR and IR spectra were in agreement with the proposed structure.

Compound (4)

N-tridecylcarbazole was prepared from carbazole (62.43 g, 0.37 mol), 1-bromotridecane (100 g, 0.38 mol), benzyltriethyl ammonium chloride (4.24 g. 0.018 mol), toluene (400 ml), and 50% aqueous NaOH (200 g) according to the procedure described for Compound (2). The product was obtained as 120 g of brown liquid (96% yield). $^1$H-NMR and IR confirmed the structure to be N-tridecylcarbazole.

N-tridecyl-3,6-diformyl carbazole was prepared from DMF (186 ml, 2.4 mol), POCl$_3$ (224 ml, 2.4 mol), and N-tridecylcarbazole (120 g, 0.34 mol) according to the procedure described for Compound (2). The product was recrystallized from THF/water to yield 130 g (84% yield) of purified product. $^1$H-NMR and IR spectra confirmed the structure to be N-tridecyl-3,6-diformylcarbazole.

Compound (4) was prepared from N-tridecyl-3,6-diformylcarbazole (130 g, 0.32 mol), N-methyl-N-phenylhydrazine (82.15 g, 0.67 mol), and concentrated HCl (5 ml) according to the procedure described for Compound (2). The product was recrystallized 3 times from toluene to is yield 100 g (50% yield) of Compound (4). $^1$H-N and IR spectra were in agreement with the structure of Compound (4).

Compound (5)

N-tetradecylcarbazole was prepared from carbazole (59.27g, 0.35 mol), 1-bromotetradecane (100 g, 0.36 mol), benzyltriethyl ammonium chloride (4.00g, 0.018 mol), 50% aqueous NaOH (200 g), and toluene (400 ml) according to the procedure described for Compound (2). The product was obtained as 120 g of a brown liquid (93% yield). Upon standing at room temperature overnight, the liquid solidified. $^1$H-NMR and IR spectra confirmed the structure to be N-tetradecylcarbazole.

N-tetradecyl-3,6-diformylcarbazole was prepared from DMF (186 ml, 2.4 mol), POCl$_3$ (224 ml, 2.4 mol), and N-tetradecylcarbazole (120 g, 0.33 mol) according to the procedure described for Compound (2). 117 g of product were obtained (84% yield). $^1$H-NMR and IR confirmed the structure to be N-tetradecyl-3,6-diformylcarbazole.

Compound (5) was prepared from N-tetradecyl-3,6-diformylcarbazole (117 g, 0.28 mol), N-methyl-N-phenylhydrazine (71.28 g, 0.58 mol), and concentrated HCl (5 ml) according to the procedure described for Compound (2). 85 g (49% yield) of Compound (5) were obtained. $^1$H-NMR and IR spectra were in agreement with the structure of Compound (5).

Compound (6)

N-propylphenylcarbazole was prepared from carbazole (82.18 g, 0.49 ml), 1-bromo-3-phenylpropane (100 g, 0.50 mol), benzyltriethyl ammonium chloride (5.58 g, 0.025 mol), toluene (400 ml), and 50% aqueous NaOH (200 g) according to the procedure described for Compound (2). 108 g of the product was obtained as a white solid (77% yield). $^1$H-NMR and IR spectra confirmed the structure to be N-propylphenylcarbazole.

N-propylphenyl-3,6-diformyl carbazole was prepared from DMF (204 ml, 2.64 mol), POCl$_3$ (246 ml, 264 mol), and N-propylphenylcarbazole (107.84 g, 0.38 mol) according to the procedure described for Compound (2). A brownish solid was obtained which was recrystallized from THF/water to yield 91.5 g (70% yield) of the product. $^1$H-NMR and IR spectra confirmed the structure to be N-propylphenyl-3,6-diformylcarbazole.

Compound (6) was prepared from N-propylphenyl-3,6-diformylcarbazole (91.5 g, 0.27 mol), N-methyl-N-phenylhydrazine (68.66 g, 0.56 mol, concentrated HCl (5 ml), and THF (900 ml total) according to the procedure described for Compound (2). A light yellow solid was obtained which was recrystallized 3 times from toluene using activated charcoal in all recrystallizations. CELITE, a diatomaceous earth material, was also used in the third recrystallization. 90 g (62% yield) of Compound (6) were obtained. $^1$H-NMR and IR spectra were in agreement with the structure of Compound (6).

Compound (7)

N-2-ethylhexylcarbazole was prepared from carbazole (85.09 g, 0.51 mol), 2-ethylhexylbromide (100 g, 0.52 mol), benzyltriethyl ammonium chloride (5.78 g, 0.025 mol), toluene (400 ml), and 50% aqueous NaOH solution (200 g) according to the procedure described for Compound (2). The product was obtained as 115 g of brownish liquid (81% yield). $^1$H-NMR and IR spectra confirmed the structure to be N-2-ethylhexylcarbazole.

N-2-ethylhexyl-3,6-diformyl carbazole was prepared from DMF (97 ml, 1.25 mol), POCl$_3$ (116.5 ml, 1.25 mol), and N-2-ethylhexylcarbazole (50 g, 0.18 mol) according to the procedure described for Compound (2). The product was obtained as 40 g of brownish liquid (66% yield). The product was used as is in the next step without any purification. $^1$H-NMR and IR spectra confirmed the structure to N-2ethylhexyl-3,6-diformyl-carbazole.

Compound (7) was prepared from N-2-ethylhexyl-3,6-diformyl-carbazole (27 g, 0.08 mol), N-methyl-N-phenylhydrazine (20.5 g, 0.17 mol), concentrated HCl (1 ml), and toluene (100 ml) according to the procedure described for Compound (2). The light yellow solid was recrystallized 3 times from toluene using activated charcoal in all three recrystallizations. Celite was also used in the third recrystallization. 25 g (56% yield) of Compound (7) were obtained. $^1$H-NMR and IR spectra were in agreement with the structure of Compound (7).

Compound (9)

To a 500 ml, three neck round bottom flask equipped with mechanical stirrer, thermometer, and addition funnel were added N-propylphenylcarbazole (56g, 0.2 mol) (prepared as described in the procedure used to prepare Compound (6)) and DMF (300 ml). The flask was placed in an ice/salt bath. When the temperature inside the flask reached 0° C., POCl$_3$ (21 ml, 0.22 mol) was added slowly by the addition funnel. The inside temperature was not allowed to rise above 5° C. during the addition of the POCl$_3$. When the addition of POCl$_3$ was completed, the flask was placed on a steam bath for 2 hr. The flask was cooled to room temperature, then added slowly to a large excess of water (2 liters in a 4.5 liter beaker). The solution was stirred at room temperature for 3 hr, the solid was filtered off, washed repeatedly with water, and followed by washing with ethanol (20 ml). The product was recrystallized once from THF/water and dried at 60° C. in a vacuum oven for 6 hr. to produce 50 g (79% yield) of N-propylphenyl-3-formylcarbazole. $^1$H-N MR and IR spectra confirmed the structure of the product.

Compound (9) was prepared from N-propylphenyl-3-formylcarbazole (50 g, 0.16 mol), N-methyl-N-phenylhydrazine (20.77 g, 0.17 mol), THF (200 mol), and concentrated HCl (1 ml) according to the procedure described for Compound (2). After heating at reflux for 4 hr. and cooling to room temperature, ethanol (100 ml) was added and the flask was stirred at room temperature overnight. The yellowish solid was filtered off and dried in a vacuum oven at 70° C. for 3 hr. The product was recrystallized three times from isopropyl alcohol, with activated charcoal used in all three recrystallizations. CELITE, a diatomaceous earth material, was also used in the third recrystallization. The product was dried in a vacuum oven at 70° C. for 6 hr. to yield 40 g (60% yield) of Compound (9). $^1$H-NMR and IR spectra were in agreement with the structure of Compound (9).

Compound (10)

Compound (10) was prepared from N-2-ethylhexyl-3-formylcarbazole (26 g, 0.084 mol, prepared as described for Compound (9)), N-methyl-N-phenylhydrazine (11 g, 0.09 mol), THF (100 ml) and concentrated HCl (1 ml) according to the procedure described for Compound (2). The product was recrystallized three times from isopropyl alcohol using activated charcoal in all three recrystallizations. CELITE, a diatomaceous earth material, was also used in the third recrystallization. 20 g (57% yield) of Compound (10) were obtained. $^1$H-NMR and IR spectra were in agreement with the structure of Compound (10).

Compound (11)

To a 5-liter, 3-neck round bottom flask equipped with mechanical stirrer and reflux condenser were added carbazole (360g, 2.15 mol), 1,10-dibromodecane (300 g, 1 mol), benzyltriethyl ammonium chloride (36 g, 0.16 mol), THF (1200 ml), and 50 % aqueous solution of NaOH (720 g). The reaction mixture was heated at reflux for 5 hr., cooled to room temperature, and stirred at room temperature overnight. The product was filtered off, washed repeatedly with water, and dried in a vacuum oven at 70° C. for 6 hr. to yield 432 g (91% yield) of a dimer.

To a 3-liter, 3-neck round bottom flask equipped with mechanical stirrer and addition funnel was added DMF (542 ml, 7 mol) and the flask was cooled in a salt/ice bath. When the temperature inside the flask reached 0 C., POCl$_3$ (652 ml, 7 mol) was slowly added using the addition funnel. The inside temperature was not allowed to rise above 5° C. during the addition of the POCl$_3$. After the addition of POCl$_3$ was complete, the flask was allowed to warm to room temperature and the dimer (237 g, 0.5 mol) was added. The flask was heated at 90° C. for 48 hr., cooled to room temperature, and added slowly to a large excess of water. The solid was isolated and recrystallized from THF/water to produce 150 g (59% yield) of the corresponding tetraaldehyde. $^1$H-NMR and IR confirmed the structure of the tetraaldehyde.

Compound (11) was prepared from the tetraaldehyde (23.46 g, 0.04 mol), N-methyl-N-phenylhydrazine (20.52 g, 0.17 mol), THF (500 ml), and concentrated HCl (5 ml) according to the procedure described for Compound (2). The product was isolated, recrystallized 3 times from toluene using activated charcoal in all three recrystallizations. CELITE, a diatomaceous earth material, was also used in the third recrystallization. 15 g (37% yield) of Compound (11) were obtained. $^1$H-NMR and IR were in agreement with the structure of Compound (11).

Compound (12)

A dimer was prepared from carbazole (35.54 g, 0.24 mol), triethylene glycol di-p-tosylate (50 g, 0.11 mol), benzyltriethyl ammonium chloride (3.77 g, 0.017 mol), toluene (200 ml), and 50% aqueous solution of NaOH (80 ml) according to the procedure described for Compound (11). 41.74 g (85% yield) of the dimer were obtained. $^1$H-NMR and IR confirmed the structure of the dimer.

The corresponding tetraaldehyde was prepared from DMF (100 ml, 1.3 mol), POCl$_3$ (122 ml, 1.3 mol), and the dimer (41.65 g, 0.09 mol) according to the procedure described for Compound (11). 20 g (38% yield) of the tetraaldehyde were obtained. $^1$H-NMR and IR confirmed the structure of the tetraaldehyde.

Compound (12) was prepared from the tetraaldehyde (11.21 g, 0.02 mol), N-methyl-N-phenylhydrazine (10.26 g, 0.084 mol), THF (300 ml), DMF (100 ml), and concentrated HCl (1 ml) according to the procedure described for Compound (11). 10 g (50% yield) of Compound (12) were obtained. $^1$H-NMR and IR spectra were in agreement with the structure of Compound (12).

B. Organic Photoreceptor Belt Preparation

A charge transport solution containing a selected charge transport compound in Polycarbonate Z binder (commercially available from Mitsubishi Gas Chemical under the designation "LUPILON Z-200" resin) was prepared by combining 120.0 g of tetrahydrofuran with 15.0 g of Polycarbonate Z, 0.03 g of DOW CORNING 510 FLUID. The resulting charge transport solution contained a charge transport compound: polycarbonate Z ratio of either 2:3 or 1:1 depending on the solubility of the charge transport compound. The charge transport solution was then die coated onto 3 mil (76 micrometer) thick polyethylene terephthalate (PET) film (MELINEX 442 polyester film from Dupont) having a 1 ohm/square aluminum vapor coat and an additional 0.25 micrometer thick PET layer overlaying the aluminum vapor coat. The purpose of including the PET overlayer was to improve adhesion and prevent charge injection into the charge transport layer. The dried charge transport layer had a nominal thickness of 8.75 micrometers. Die coating (also known as slot coating techniques are described by E. Cohen and E. Gutoff, *Modern Coating and Drying Technology*, VCH Publishers, Inc. New York, 1992, pp. 117–120.

A dispersion was prepared by micronising 32.6 g of PROGEN X-form metal free phthalocyanine pigment (Zeneca Inc.), 32.6 g of S-LEC B BX-5 polyvinyl butyral resin (Sekisui Chemical Co. Ltd.), and 684.4 g of 2/1 (v/v) methyl ethyl ketone/toluene using a horizontal sand mill operating in recirculation mode for 8 hours. This stock solution was diluted to 3.5 wt. % solids by adding 1113 g of 2/1 (v/v) methyl ethyl ketone/toluene prior to coating. The resulting dispersion was die coated onto the charge transport layer and dried to form a charge generating layer having a nominal thickness of 0.27 micrometer. This dual layer organic photoconductor was then overcoated with a barrier layer.

Two different barrier layer solutions were used. The first ("Barrier A") was prepared by mixing 86.3 g of 3% methyl cellulose available under the trade designation METHOCEL A15LV in water, 86.3 g of 3% methylvinylether/maleic anhydride copolymer available under the trade designation GANTREZ AN-169 polymer (ISP Technologies) in water, 172.44 g of methanol, 0.65 g of 40% GLYOXAL 40 in water, and 0.07 g TRITON X-100 non-ionic surfactant following the procedure described in Ackley et al., "Organic Photoreceptors for Liquid Electrophotography," U.S. Pat. No. 6,180,305 B1, filed Feb. 16, 2000 and assigned to the same assignee as the present application. The other barrier layer solution ("Barrier B") was prepared by combining 217.6 g of 6% S-LEC BX-5 polyvinyl butyral resin, 1385.7 g isopropyl alcohol, 33.5 g NALCO 1057 colloidal silica, 33.1% Z-6040 Silane (Dow Corning 50/50 in isopropyl alcohol/water), and 130.17 g GANTREZ AN169 methylvinylether/maleic anhydride copolymer following the procedure described in U.S. Pat. No. 5,733,698.

The barrier layer solution was die coated onto the dual layer organic photoconductor and dried to form a layer having a nominal thickness of 0.4 micrometer.

C. Thermal Transitions

Thermal transition data for various charge transport materials was collected using a TA Instruments Model 2929 Differential Scanning Calorimeter (New Castle, Del.) equipped with a DSC refrigerated cooling system (−70° C. minimum temperature limit), and dry helium and nitrogen exchange gases. The calorimeter ran on a Thermal Analyst 2100 workstation with version 8.10B software. An empty aluminum pan was used as the reference.

Samples were tested both neat and as a mixture with Polycarbonate Z ("PCZ"). The neat samples were prepared by placing 4.0 to 8.0 mg of neat charge transport material into an aluminum sample pan and crimping the upper lid to produce a hermetically sealed sample for DSC testing. The results were normalized on a per mass basis.

The Polycarbonate Z-mixed samples were prepared by filling the bottom portion of the aluminum sample pan to capacity with a 15–20% solids solution of the charge transport material in Polycarbonate Z, followed by air-drying overnight. Each air-dried sample was then placed in a convection oven at 50–55° C. for another 24–48 hours to eliminate trace solvent after which the upper sample lid was crimped on to produce a hermetically sealed sample for DSC testing. Typical sample size was 7.0 to 15.0 mg. Again, the results were normalized on a per mass basis.

Each sample was subjected to the following protocol to evaluate its thermal transition behavior:

1. Equilibrate at 0° C. (Default-Nitrogen Heat Exchange Gas);
2. Isothermal for 5 min.;
3. External Event: Nitrogen Heat Exchange Gas;
4. Ramp 10.0° C./min. to a temperature 30° C. above the CTM's melting point;
5. External Event: Helium Heat Exchange Gas;
6. Isothermal for 5 min.;
7. Ramp 10.0° C./min. to 0° C.;
8. External Event: Nitrogen Heat Exchange Gas;
9. Isothermal for 5 min.;
10. Ramp 10.0° C./min. to a temperature 40° C. above the CTM's melting point;
11. External Event: Helium Heat Exchange Gas;
12. Isothermal for 5 min.;
13. Ramp 10.0° C./min. to 0° C.;
14. External Event: Nitrogen Heat Exchange Gas;
15. Isothermal for 5 min.;
16. Ramp 10.0° C./min. to 275° C.

The first cycle (steps 1–7) was used to (a) remove the thermal history of the sample, (b) obtain the melting transition for crystalline charge transport materials, and (c) obtain a homogeneous charge transport material/Polycarbonate-Z mixture in the event the charge transport material crystallized during sample preparation. A homogeneous mixture is obtained only if the charge transport material (melt or cast) is miscible with the Polycarbonate-Z.

The second cycle (steps 8–13) was used to identify the glass transition temperature and charge transport material recrystallization or melting transitions.

The third cycle (steps 14–16) was used to report the final thermal transitions.

The results are shown below in Table 1. All temperatures are reported in °C. "CTM" the charge transport material (i.e., the charge transport compound, as used above). "PCZ" refers to Polycarbonate Z.

TABLE 1

| | NEAT CTM | | | |
|---|---|---|---|---|
| CTM | Melting Temperature (Tm) | Glass Transition Temperature (Tg) | CTM/PCZ CTM:PCZ Ratio | Glass Transition Temperature (Tg) |
| 3 | 180 | None | 2:3 | 87 |
| 4 | 165 | None | 2:3 | 73 |
| 5 | 170 | None | 2:3 | 83 |
| 6 | 241 | 64 | 2:3 | 106 |
| 7 | 197 | 59 | 2:3 | 100 |
| 9 | 124 | 32 | 1:1 | 55 |
| 10 | 100–115 | 12 | 1:1 | 46 |
| 11 | 129 | 91 | 2:3 | — |
| 12 | 134 | 102 | 2:3 | 133 |

In general, it is desirable to maximize the glass transition temperature, while at the same time maximizing solubility in the binder, in order to minimize environmental stress cracking that can occur when the organic photoreceptor is brought into contact with organic carrier liquids used in liquid toners.

D. Photo Induced Discharge Curves (PIDC)

Organic photoreceptor belts were prepared as described above. Each belt measured 50 cm long by 8.8 cm wide and was fastened to an aluminum drum having a circumference of 50 cm. The drum rotated at a rate of 7.6 cm/min. Corona charging and discharging stations were positioned around the drum.

Each belt was charged up to 500 V, stopped under an optical probe, and then discharged using a Xenon Flash lamp (XENON 456 Micropulser, Xenon Corp. Woburn, Mass.). Belts that were unable to attain 500 V were charged up to the maximum attainable charge acceptance voltage. The flash generated by the micropulser passed through a 780 nm optical filter, traveled through the optical probe, and discharged the area of the belt under the probe. Data was collected at a rate of 2000 samples per second for 2 seconds, and processed using Labview™ software before being downloaded to a spread sheet and graphing application. Measurements were taken at both 25° C. and 40° C.; the latter temperature was obtained using a heating element inside the aluminum drum.

The rate at which each charge transport layer lost its charge was determined as follows. The discharge rate at the initial maximum voltage, $t(V_i)$, was taken as the amount of time required for the initial acceptance voltage ($V_i$) to drop to one-half of its value. The discharge rate is proportional to the initial acceptance voltage. Therefore, to compare samples on an equal basis, the discharge rates for belts made from different charge transport materials were then normalized to values that would have been obtained if the initial belt voltage charged up to 500 V by using the equation:

$$t_{500V} = t(V_i) * (V_i/500)$$

As a first approximation, the voltage across the thin barrier layer was insignificant as compared to the much thicker charge generating and charge transport layers. This implies that the 500V drop across the sample can be attributed to the charge generating and charge transport layers, and that all samples can be compared on an equal basis.

The residual potential voltage ($V_{res}$), was measured 310 milliseconds after the XENON Micropulser flash. This time interval was selected because it matches a key process time in a printer during actual use. The results are shown in Table 2 for organic photoreceptors incorporating various charge transport compounds. All values for $t_{500V}$ are reported in milliseconds. All values for $V_i$ and $V_{res}$, are reported in volts.

TABLE 2

| CTM | Barrier | $V_i$ @ 25° C. | $t_{500V}$ @ 25° C. | $V_{res}$ @ 25° C. | $V_i$ @ 40° C. | $t_{500V}$ @ 40° C. | $V_{res}$ @ 40° C. | ratio $T_{500V}$ 25° C./40° C. |
|---|---|---|---|---|---|---|---|---|
| 3 | None | 150 | 62.5 | 68 | 122 | 17.2 | 46 | 3.6 |
| 4 | None | 344 | 10.8 | 110 | 368 | 0.3 | 38 | 36.0 |
| 5 | None | 389 | 12.3 | 124 | 372 | 2.1 | 75 | 5.9 |
| 7 | A | 495 | 0.8 | 17 | 370 | 0.6 | 11 | 1.3 |
| 9 | B | 508 | 8.0 | 139 | 517 | 3.0 | 113 | 2.7 |
| 10 | A | 491 | 3.7 | 33 | 408 | 1.7 | 22 | 2.2 |

In general, it is desirable to minimize values of both $V_{res}$ and $t_{500}$, while maximizing $V_i$. The data in Table 2 demonstrate that based upon these criteria, the performance of each organic photoreceptor was acceptable, and that photoreceptors based upon charge transport compounds (7) and (10) gave the best performance.

E. Mixtures of Charge Transport Compounds

Coating solutions were prepared by mixing charge transport compound (8 wt. %), Polycarbonate Z-200 (12 wt. %), tetrahydrofuran (80 wt. %), and DC 510 (0.019 wt. %), and heating the mixture with a hot air gun to ensure homogeneity. After standing for approximately one hour, the sample equilibrated to room temperature to yield a clear, homogeneous solution. The solution was then hand coated using a wire-wound rod (Meyer Bar #36) onto a piece of aluminized PET measuring 12 inches by 8 inches to form a charge transport layer. A 0.2 micron thick polyester adhesion layer was applied to the aluminum side of the sheet prior to coating. Immediately following coating, the sample was dried in a oven at 80° C. for 5 minutes, and then at 100° C. for 2 minutes. A metal-free phthalocyanine charge generating layer was then laminated onto the dried charge transport layer to produce the organic photoconductor.

Electrostatic testing of each sample was performed and recorded on a QEA PDT-2000 instrument at room temperature. Table 3 lists the schedule of events per cycle and the appropriate definitions for this particular test procedure.

TABLE 3

| Event | Measured Voltage | Time (sec) | Definition | Definition |
|---|---|---|---|---|
| Cycle Start | $V_0$ | 0.00 | Charge Acceptance Voltage | $V_{acc} = V_0$ |
| PreExpose | $V_1$ | 1.00 | Dark Decay | $V_{dd} = V_0-V_1$ |
| Expose Start | $V_2$ | 1.00 | | |
| Expose End | $V_3$ | 1.05 | Initial Discharge Rate | $Idr = (V_2-V_3)/0.05$ sec |
| PreErase | $V_4$ | 2.05 | Contrast Voltage | $V_{cont} = V_1-V_4$ |

TABLE 3-continued

| Event | Measured Voltage | Time (sec) | Definition | Definition |
|---|---|---|---|---|
| Erase | $V_5$ | 2.05 | | |
| Cycle End | $V_6$ | 3.00 | Residual Voltage | $V_{res} = V_6$ |

For each charge-discharge cycle, the sample, which was adhered to the instrument drum, was charged up using a positive corona grid and the voltage recorded as the charge acceptance voltage ($V_{acc}$). After 1 second, the sample was discharged by an external, 780 nm pass-band filtered, tungsten light source that was connected to the instrument via a fiber optic cable. Each sample was exposed to 2 $\mu J/cm^2$ of energy for 0.05 sec. at a total exposure intensity of 20 $\mu W/cm^2$. The drop in voltage during the first second after charging, but before light exposure, was recorded as the dark decay value for the sample ($V_{dd}$).

The drop in voltage during the 0.05 sec. exposure to the 780 nm imaging light was recorded as the initial discharge rate for the sample. The contrast voltage ($V_{cont}$) was obtained prior to the sample being completely erased (1 second before exposure end). The residual voltage ($V_{res}$) was recorded 0.95 sec. after erasure. The sample was then recharged for the beginning of the next cycle. Table 4 summarizes the average values obtained over 100 cycles.

TABLE 4

| CTM | $V_{acc}$ (volts) | $V_{dd}$ (volts) | $V_{cont}$ (volts) | $V_{res}$ (volts) |
|---|---|---|---|---|
| 7 | 455 | 158 | 223 | 78 |
| 3 | 583 | 86 | 378 | 97 |
| 4 | 386 | 59 | 148 | 76 |
| 5 | 506 | 73 | 338 | 77 |
| 7 + 3 (1:1) | 610 | 159 | 392 | 48 |
| 7 + 4 (1:1) | 616 | 124 | 446 | 37 |
| 7 + 5 (1:1) | 588 | 142 | 357 | 42 |

In general, it is desirable to maximize $V_{acc}$ and $V_{cont}$, while minimizing $V_{res}$ and $V_{dd}$. The data in Table 4 demonstrate that, while the performance of each organophotoreceptor was acceptable, mixtures of charge transport compounds performed even better than the individual charge transport compounds alone.

All patents, patent applications, and publications disclosed herein are incorporated by reference in their entirety, as if individually incorporated. The foregoing detailed description and examples have been given for clarity of understanding only. No unnecessary limitations are to be understood therefrom. The invention is not limited to the details shown and described, for variations obvious to one skilled in the art will be included within the invention defined by the claims.

What is claimed is:

1. An organic photoreceptor comprising:
(a) a charge transport compound having the formula

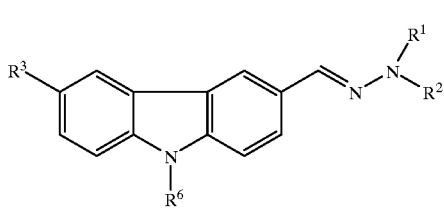
(1)

where $R^1$ and $R^2$, independently, are hydrogen, an alkyl group, or an aryl group;
$R^3$ is hydrogen or a hydrazone group having the formula

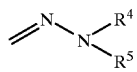

$R^4$ and $R^5$, independently, are hydrogen, an alkyl group, or an aryl group;
$R^6$ is an aryl group; straight or branched alkyl group having at least 7 carbon atoms; a group having the formula —$(CH_2)_n$—Ar where n is at least 3, Ar represents an unsubstituted aryl group, and one or more methylene groups is optionally substituted with a heteroatom; or a carbazole group having the formula

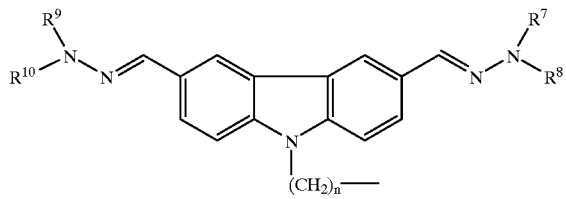

where $R^7$, $R^8$, $R^9$, and $R^{10}$, independently, are hydrogen, an alkyl group, or an aryl group; n is at least 3; and one or more methylene groups is optionally substituted with a heteroatom, with the proviso that when $R^3$ is hydrogen, $R^6$ is not an aryl group;
(b) a charge generating compound; and
(c) an electroconductive substrate.

2. An organic photoreceptor according to claim 1 wherein said organic photoreceptor is in the form of a flexible belt.

3. An organic photoreceptor according to claim 1 comprising:
(a) a charge transport layer comprising at least one of said charge transport compounds and a polymeric binder;
(b) a charge generating layer comprising said charge generating compound and a polymeric binder; and
(c) said electroconducting substrate.

4. An organic photoreceptor according to claim 3 wherein said charge transport layer has a glass transition temperature of at least about 80° C.

5. An organic photoreceptor according to claim 3 wherein said charge transport layer comprises two of said charge transport compounds in a ratio with one another of about 9:1 to about 1:1 mixture by weight.

6. An organic photoreceptor according to claim 3 wherein said charge transport layer is intermediate said charge generating layer and said electroconductive substrate.

7. An organic photoreceptor according to claim 3 wherein said charge generating layer is intermediate said charge transport layer and said electroconductive substrate.

8. An organic photoreceptor according to claim 1 wherein $R^3$ is the hydrazone group having the formula recited in claim 1, where $R^4$ is a methyl group, and $R^5$ is a phenyl group.

9. An organic photoreceptor according to claim 1 wherein said charge transport compound is selected from the group consisting of

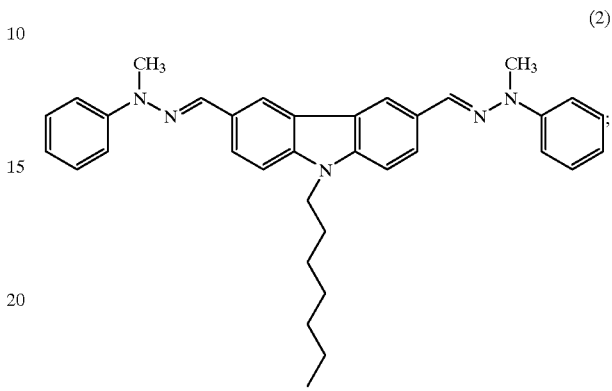
(2)

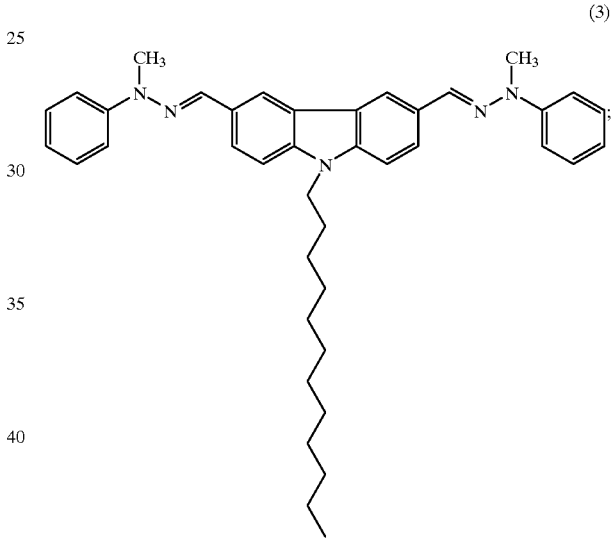
(3)

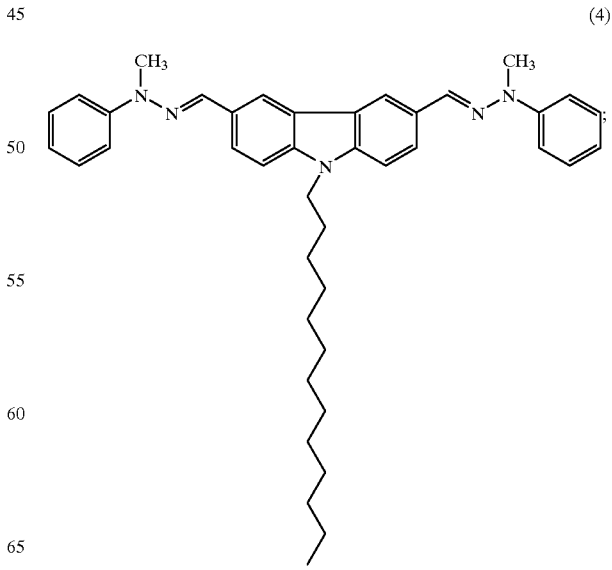
(4)

(5)
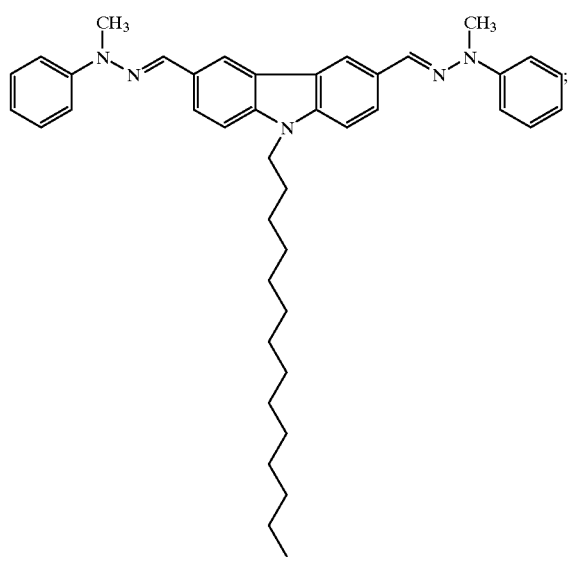
(6)
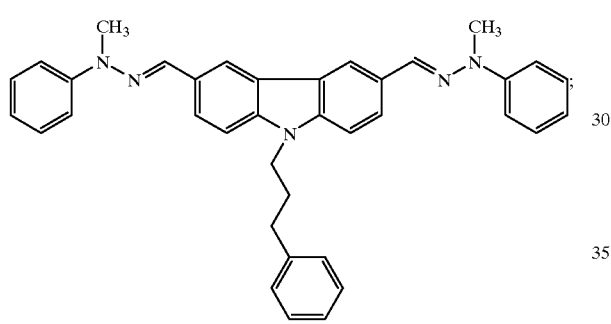
(7)
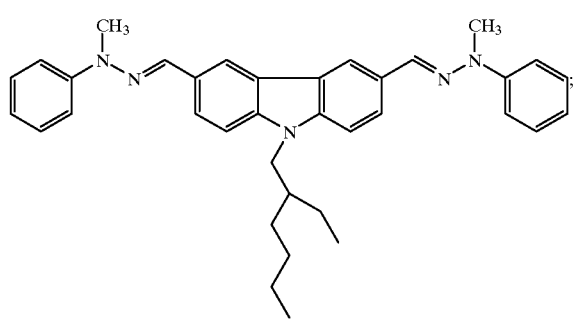
(9)
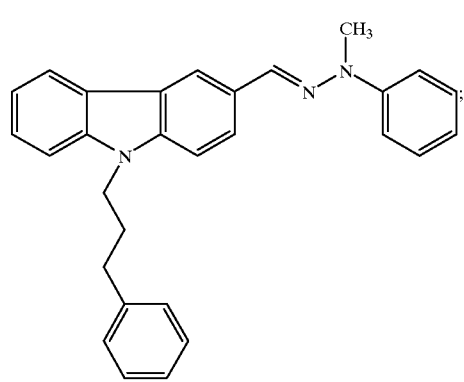
(10)
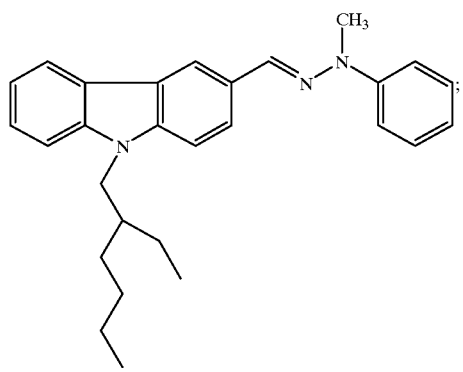
(11)
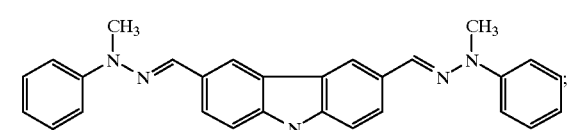
(12)
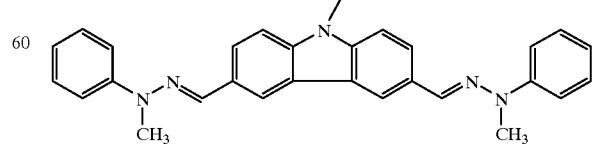
and combinations therof.

10. An electrophotographic imaging apparatus comprising:

(a) a plurality of support rollers; and
(b) an organic photoreceptor in the form of a flexible belt supported by said support rollers,
said organic photoreceptor comprising:
(i) a charge transport compound having the formula

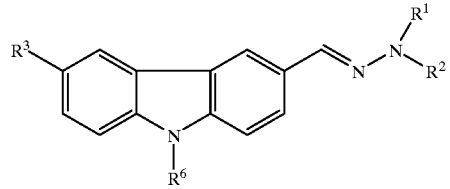

(1)

wherein $R^1$ and $R^2$, independently, are hydrogen, an alkyl group, or an aryl group;
$R^3$ is hydrogen or a hydrazone group having the formula:

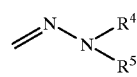

$R^4$ and $R^5$, independently, are hydrogen, an alkyl group, or an aryl group;
$R^6$ is an aryl group; a straight or branched alkyl group having at least 7 carbon atoms; a group having the formula —(CH$_2$)$_n$—Ar where n is at least 3, Ar represents an unsubstituted aryl group, and one or more methylene groups is optionally substituted with a heteroatom; or a carbazole group having the formula

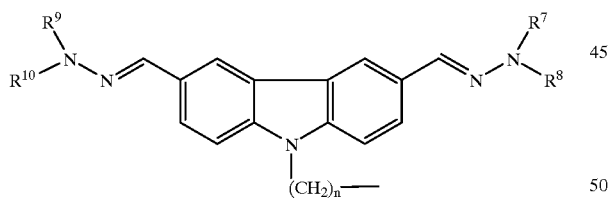

where $R^7$, $R^8$, $R^9$, and $R^{10}$, independently, are hydrogen, an alkyl group, or an aryl group; n is at least 3; and one or more methylene groups is optionally substituted with a heteroatom, with the proviso that when $R^3$ is hydrogen, $R^6$ is not an aryl group;
(ii) a charge generating compound; and
(iii) an electroconductive substrate.

11. An apparatus according to claim 10 wherein at least one of said support rollers has a diameter no greater than about 40 mm.

12. An apparatus according to claim 10 wherein said charge transport compound is selected from the group consisting of

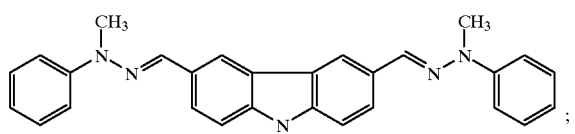

(2)

(3)

(4)

(5)
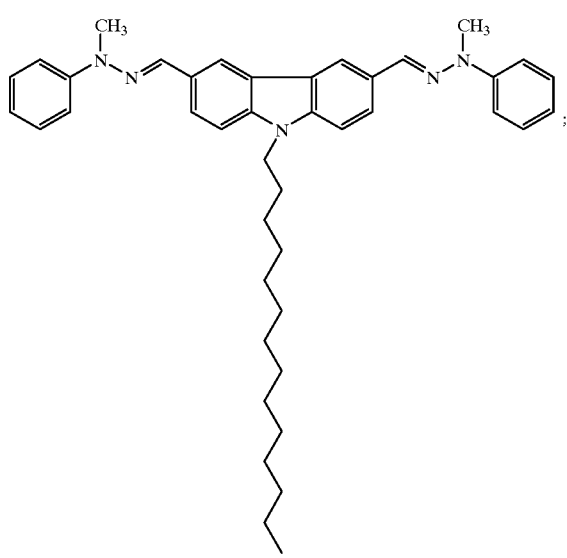
(6)
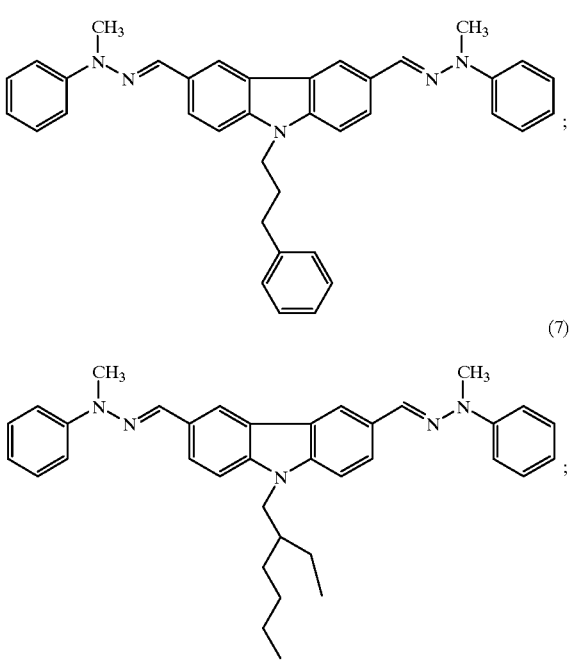
(7)
(9)
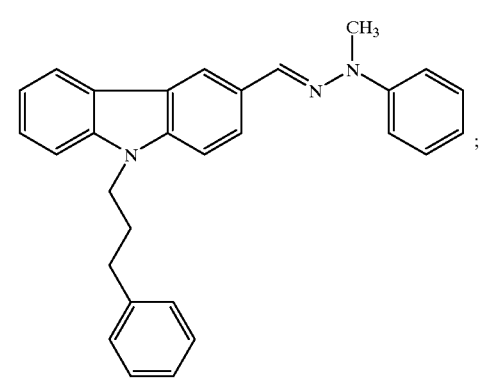
(10)
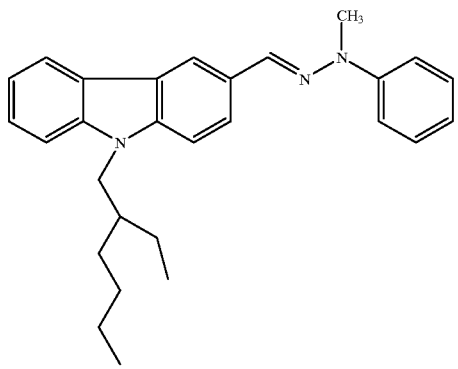
(11)
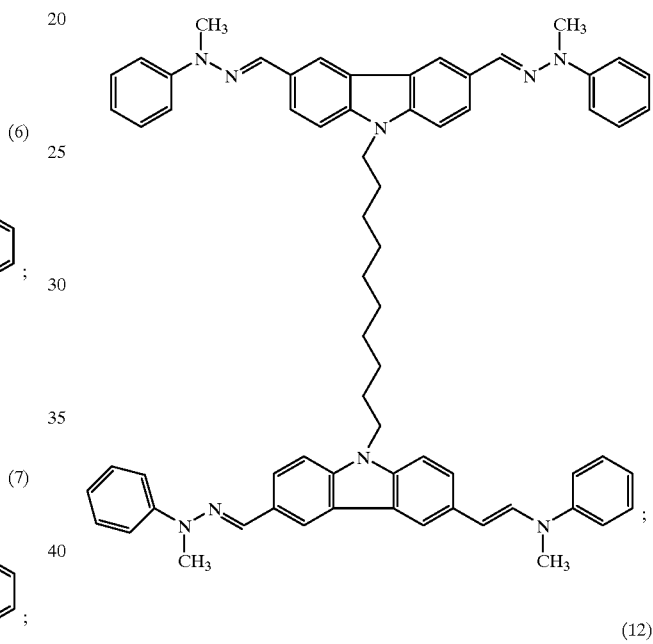
(12)
and combinations thereof.

13. A charge transport compound having the formula:

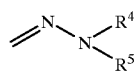

where $R^1$ and $R^2$, independently, are hydrogen, an alkyl group, or an aryl group;

$R^3$ is hydrogen or a hydrazone group having the formula

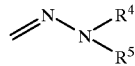

$R^4$ and $R^5$, independently, are hydrogen, an alkyl group, or an aryl group;

$R^6$ is an aryl group; a straight or branched alkyl group having at least 7 carbon atoms; a group having the formula —$(CH_2)_n$—Ar where n is at least 3, Ar represents an unsubstituted aryl group, and one or methylene groups is optionally substituted with a heteroatom; or a carbazole group having the formula

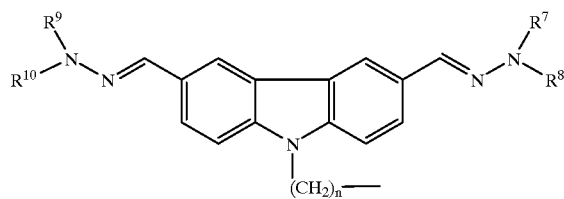

where $R^7$, $R^8$, $R^9$, and $R^{10}$, independently, are hydrogen, an alkyl group, or an aryl group, n is at least 3; and one or methylene groups is optionally substituted with a heteroatom, with the proviso that when $R^3$ is hydrogen, $R^6$ is not an aryl group.

* * * * *